United States Patent [19]
Ettlin et al.

[11] Patent Number: 6,005,075
[45] Date of Patent: Dec. 21, 1999

[54] METHOD FOR PRODUCING ALPHA-INTERFERON

[75] Inventors: Urs Ettlin, Basle; Erich Hochuli, Arisdorf; Alfred Schacher, Riehen, all of Switzerland; Karl Weyer, Bad Bellingen, Germany

[73] Assignee: Hoffmann-La Roche Inc., Nutley, N.J.

[21] Appl. No.: 08/899,037

[22] Filed: Jul. 23, 1997

Related U.S. Application Data

[63] Continuation of application No. 08/417,316, Apr. 5, 1995, abandoned.

[30] Foreign Application Priority Data

Apr. 9, 1994 [WO] WIPO ................................. 94105532

[51] Int. Cl.$^6$ ............... C07K 1/14; C07K 1/16; C07K 1/30; C07K 14/56
[52] U.S. Cl. ............ 530/351; 530/412; 530/415; 530/418; 530/419
[58] Field of Search ................. 530/412, 415, 530/418, 419, 351; 424/85.7

[56] References Cited

U.S. PATENT DOCUMENTS

| | | | |
|---|---|---|---|
| 4,485,038 | 11/1984 | Chaha et al. | 260/112 K |
| 4,551,271 | 11/1985 | Hochuli | 260/112 R |
| 4,620,948 | 11/1986 | Builder et al. | |
| 4,828,990 | 5/1989 | Higashi et al. | 435/68 |

FOREIGN PATENT DOCUMENTS

| | | |
|---|---|---|
| 0043980 | 1/1982 | European Pat. Off. |
| A-0 203 382 | 4/1986 | European Pat. Off. |
| 0211148 | 2/1987 | European Pat. Off. |
| 211148 | 2/1987 | European Pat. Off. |
| 553494 A1 | 8/1993 | European Pat. Off. |
| A 92 10207 | 6/1992 | WIPO |

OTHER PUBLICATIONS

Hochuli, Large–Scale Recovery of Interferon –2a Synthesized in Bacteria, Chima, vol. 40, pp. 408–412, 1986.

Thatcher et al., "Purification of Recombinant Human IFN–alpha–2", Purification of interferons, part C pp. 166–177, 1986.

Gail Sofer and V. J. Britton, Bio Techniques, pp. 198–203 (Nov./Dec. 1983).

Staehelin et al., J. of Biological Chemistry, vol. 256, No. 18, pp. 9750–9754 (1981).

Staehelin et al., Methods in Enzymology, vol. 78, pp. 505–512 (1981).

Tarnowski et al., Advances in Biotechnological Process 2, pp. 271–287 (1983).

J. K. Lee, et al., Korean Biochem. Journal, vol. 25, No. 1, pp. 73–78 (1992).

W. G. Lewis et al., Interferon, vol. 1, pp. 251–256 (1984).

D. R. Thatcher et al., Methods in Enzymology, vol. 119, pp. 166–177 (1986).

Gray, et al, Expression of human interferon cDNA in *E. coli* and monkey cell, Nature, vol. 295, (1992).

Nagata, et al, Synthesis in *E. coli* of a polypeptide with human keukocyte interferon activity, Nature, vol. 284 (1980).

Staehelin, et al, Purification and Characterization of Recombinant Human Leukocyte Interferon (IFlrA) with Monoclonal Antibodies, The J. Biol. Chem., vol. 256, No. 18 pp. 9750–9754 (1981).

Goeddel, et al, The structure of eight distinct cloned human leukocyte interferon cDNAs, Nature, vol. 290, (1981).

Secher, et al, A monoclonal antibody for large–scale purification of human leukocyte interferon, Nature, vol. 285, (1980).

Goeddel, et al, Synthesis of human fibroblast interferon by *E. coli*, Nucleic Acids Research, vol. 8, No. 18, (1980).

Hochuli, Large–scale Recovery of Interferon α–2a Synthesized in Bacteria, Chima, vol. 40 (1986).

*Primary Examiner*—Cecilia J. Tsang
*Assistant Examiner*—Anish Gupta
*Attorney, Agent, or Firm*—George W. Johnston; Dennis P. Tramaloni; Joseph P. Kirk, Jr.

[57] ABSTRACT

The invention provides processes for producing Alpha-Interferon (IFN-α) free from possible mouse and/or virus contamination. The present invention further provides homogeneous IFN-α free from mouse and/or virus contamination and its use in antitumor and/or antiviral treatment.

27 Claims, 3 Drawing Sheets

METHOD FOR PRODUCING ALPHA-INTERFERON

This is a continuation of application Ser. No. 08/417,316, filed Apr. 5, 1995 now abandoned.

BACKGROUND OF THE INVENTION

The present invention is concerned with a process for producing Alpha-Interferon (IFN-α) in which chromatography on immunosorbents, namely on anti-interferon antibodies, is avoided in favour of anion exchange chromatography, the protein itself and the use thereof. The new process avoids (a) any virus contamination of the final product which might occur, and (b) a bottleneck in the production process caused by the use of antibody column.

Interferons are proteins naturally occurring in the body which have antiviral, antiproliferative and immunoregulatory activity. The antiviral effect is achieved not by a direct influence on the viruses themselves, but by an activity on their target cells in the sense of a protection against the virus infection. The interferons can exert objectifiable effects on cancer tumours, which make them suitable for use in cancer therapy, and they can influence the immune system of the body on that, for example, they activate macrophages and NK cells and intensify the expression of various immunologically significant constituents of the cell membrane.

Human interferons (alpha, beta and gamma) can today be prepared in a microbiological manner thanks to recombinant DNA technology in amounts which cannot be made available by isolation from natural material (leucocytes, fibroblasts, lymphocytes) and purification in spite of the greatest efforts.

This technology has opened a way for the intensive clinical testing and wide therapeutic use of interferons by providing an adequate supply of the active substances.

Details of the cloning of interferon-cDNA and the direct expression thereof, especially in *E. coli*, have in the meantime been the subject of many publications. Thus, for example, the preparation of recombinant interferons is known, for example, from *Nature*, 295 (1982), 503–508, *Nature*, 284 (1980), 316–320, *Nature*, 290 (1981), 20–26, *Nucleic Acids Res.*, 8 (1980), 4057–4074, as well as from European Patents Nos. 32134, 43980 and 211 148.

Since the recombinant interferons are of microbial origin (e.g., they are preferably derived from *E. coli*), after their isolation from the microorganism or from the culture medium they are initially still contaminated by a series of microbial impurities, the presence of which is prohibitive for a therapeutic use of the thus-produced interferons. The purification of the recombinant material therefore plays a particularly important role. A multitude of different methods, especially chromatography, have hitherto been used and combined with one another for the purification of recombinant interferons. Above all, chromatography on immunoadsorbents, namely on anti-interferon antibodies, has proved to be a valuable aid. Thus, the purification of recombinant human leucocyte interferon (HuIFN-α) by means of monoclonal antibodies has been described, for example, by Staehelin et al. (*J.Biol.Chem.*, 256 (1981), 9750–9754) and by Secher et al. (*Nature*, 285 (1980), 446–450). Having regard to the high specificity of these immunoadsorbents it must be assumed from this that the thus-purified material is practically free from contaminating substances and has a high degree of purity.

In the case of the purification of larger amounts of recombinant IFN-α by means of monoclonal antibodies it has, however, been found that the purified material contains not only interferon fragments (interferon in which a part of the terminal amino acid sequence is missing), but also interferon oligomers, for example, dimers. These undesirable by-products prompted the inclusion of additional chromatography steps in the purification process.

A method for producing IFN-α using immunoaffinity chromatography followed by copper chelate chromatography and cation exchange chromatography has been described in *Chimia*, 40 (1986) 408–412. However, the use of immunoaffinity chromatography may be accompanied by the problem of mouse immunoglobulin and virus contamination in the final product. Mouse immunoglobulin contamination could occur due to trace amounts of immobilized antibody being eluted with the final product. Viral contamination could occur due to bovine serum being used in the production of the monoclonal antibodies. Additionally, it has been found that this method is limited in scale since several runs on the antibody column are needed for one full batch.

DETAILED DESCRIPTION OF THE INVENTION

Figures 1A, 1B, 1C:
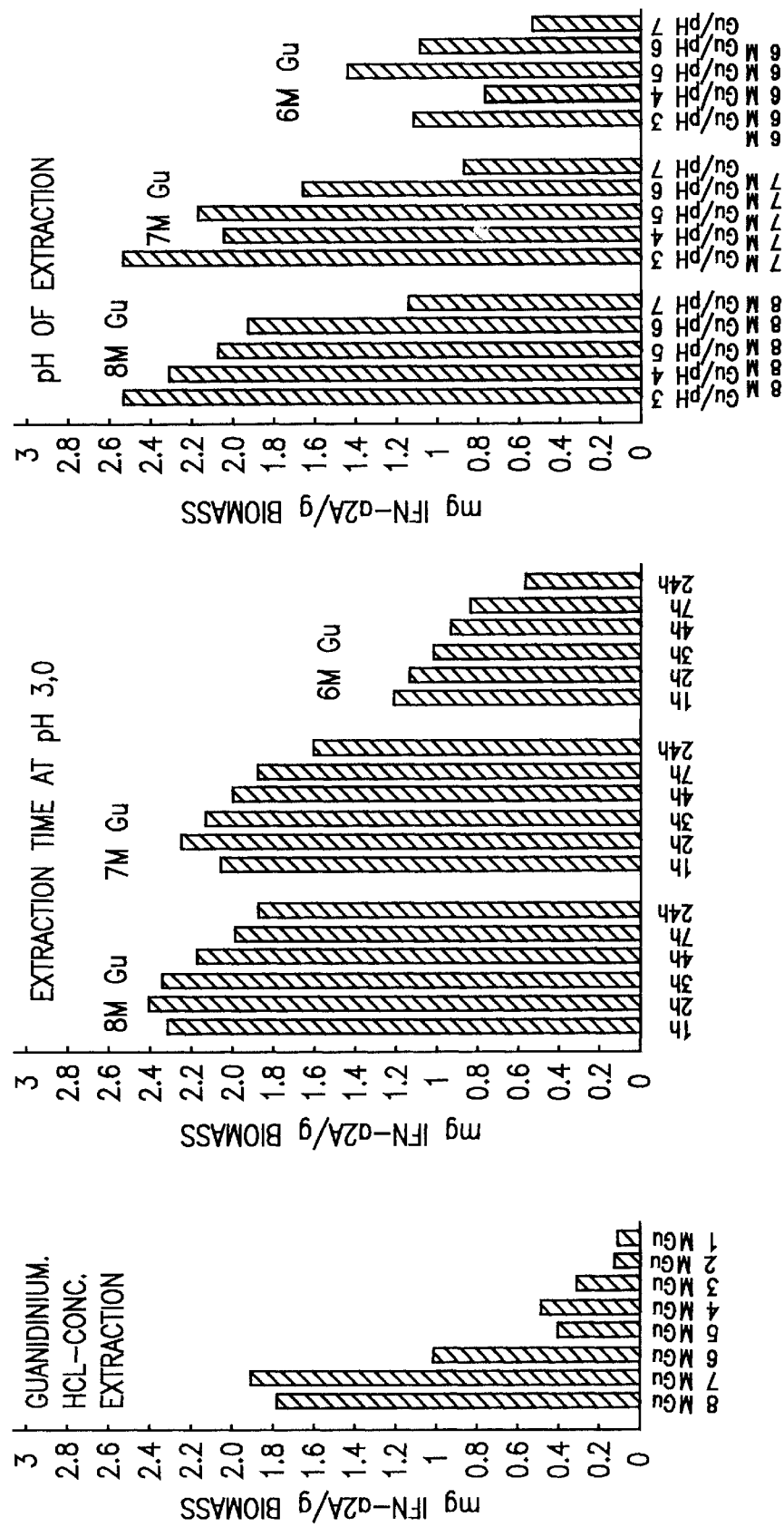
FIG. 1 shows the results of IFN-α2A extraction subject to guanidinium concentration (A) extraction time (B) and extraction pH-values (C).

In accordance with the present invention it has now been found that homogeneous IFN-α, free from possible mouse immunoglobulin and/or virus contamination, can be obtained in high yield by using in place of the immunoaffinity chromatography, e.g., described in *Chimia*, supra, anion exchange chromatography, especially quaternary aminoethyl anion exchange chromatography.

Surprisingly, it has also been found that the conditions of the extraction of the expressed IFN-α using a chaotropic agent, for example, a guanidinium salt, followed by dilution of the extraction solution using water or an aqueous buffer also increase the yield of IFN-α.

Accordingly, the present invention is concerned with a process allowing the production and purification of homogeneous IFN-α, which process comprises the steps of:

(a) cultivating a host containing a IFN-α gene to express IFN-α;

(b) extracting the expressed IFN-α using a chaotropic agent;

(c) re-folding the extracted IFN-α by diluting with water or an aqueous buffer solution;

(d) subjecting the IFN-α to metal chelate chromatography;

(e) subjecting the metal chelate purified IFN-α to cation exchange chromatography;

(f) subjecting the IFN-α eluted from the cation exchange chromatography column to anion exchange chromatography; and (g) passing the interferon eluted from the anion exchange chromatography column through a gel filtration column.

It is also possible to successfully employ hydrophobic interaction chromatography instead of metal chelate chromatography in step (d) of the process of the present invention. Additionally, it is possible to successfully employ first cation exchange chromatography followed by metal chelate chromatography or to exchange the sequence of the ion exchange column steps in the process of the present invention.

Thus, the invention comprises a process for purifying IFN-α to homogeniety from an aqueous solution containing IFN-α and other co-produced proteins extracted from a recombinant cell culture which expresses IFN-α, where the proteins in said solution have been subjected to metal chelate chromatography or hydrophobic interaction chromatography, and to cation exchange chromatography, comprising:

(a) passing the aqueous solution containing the IFN-α through an anion exchange chromatography column whereby the IFN-α is captured on said column and eluting the IFN-α from said column with a first aqueous buffer solution to obtain IFN-α in said first aqueous buffer solution; and (b) thereafter passing said first aqueous buffer solution obtained from step (a) containing the IFN-α through a gel filtration chromatography column whereby the IFN-α is captured on said column and eluting the IFN-α from said column with a second aqueous buffer solution to obtain homogenous IFN-α in said second aqueous buffer solution.

In one embodiment in accordance with the invention, the aqueous solution containing the IFN-α and other co-produced proteins has been subjected to metal chelate chromatography and to cation exchange chromatography prior to the anion exchange chromatography step. Preferably, the metal chelate chromatography is carried out prior to the cation exchange chromatography. However, in accordance with the invention the cation exchange chromatography may be carried out prior to the metal chelate chromatography. The preferred metal chelate chromatography is copper chelate chromatography.

In another embodiment of the invention, the aqueous solution containing the IFN-α and other co-produced proteins has been subjected to hydrophobic interaction chromatography and to cation exchange chromatography prior to the anion exchange chromatography step. Preferably, the hydrophobic interaction chromatography is carried out prior to the cation exchange chromatography. However, in accordance with the invention the cation exchange chromatography may be carried out prior to the hydrophobic interaction chromatography The process of the invention may also be carried out by performing the anion exchange chromatography prior to the cation exchange chromatography. Thus, the invention also comprises a process for purifying IFN-α to homogeniety from an aqueous solution containing IFN-α and other co-produced proteins extracted from a recombinant cell culture which expresses IFN-α, where the proteins in said solution have been subjected to metal chelate chromatography or hydrophobic interaction chromatography, comprising:

(a) passing the aqueous solution containing the IFN-α through an anion exchange chromatography column whereby the IFN-α is captured on said column and eluting the IFN-α from said column with a first aqueous buffer solution to obtain IFN-α in said first aqueous buffer solution;

(b) thereafter passing said first aqueous buffer solution obtained from step (a) containing the IFN-α through a cation exchange chromatography column whereby the IFN-α is captured on said column and eluting the IFN-α from said column with a second aqueous buffer solution to obtain IFN-α in said second aqueous buffer solution; and (c) thereafter passing said second aqueous buffer solution obtained from step (b) containing the IFN-α through a gel filtration chromatography column whereby the IFN-α is captured on said column and eluting the IFN-α from said column with a third aqueous buffer solution to obtain homogenous IFN-α in said third aqueous buffer solution.

The preferred anion exchange chromatography for use in accordance with the present the invention is quarternary aminoethyl anion exchange chromatography. The aqueous buffer solution used to elute the IFN-α from the anion exhange resin in accordance with the present invention is preferably an aqueous acetate buffer solution. The elution of the IFN-α from the anion exchange resin is preferably carried out by varying the pH of the aqueous buffer solution during the elution (a pH gradient), starting with a buffer having a pH of about 6 and reducing the pH during elution to a pH of about 4.5.

The preferred interferon to be purified in accordance with the present invention is IFN-α2A.

As already stated above, the process of the present invention is particularly suitable for the preparation of pure and homogeneous IFN-α free from possible mouse immunoglobulin and/or virus contamination in high yield. Additionally, the process of the present invention shows improved reproducibility due to a larger production scale as compared to the process described in *Chimia,* supra. With the process of the present invention a full batch can be processed in one step in all process steps whereas in the process described in *Chimia,* supra, 3–6 separate runs on the immunoaffinity column are needed for one full batch. Moreover, by replacing the immunoaffinity chromatography improved hygiene in the manufacturing process can be achieved since all columns can be sanitized, e.g., with sodium hydroxide and, furthermore, there is no need for chemicals, such as sodium thiocyanate and Triton X-100, which are not considered as pharmaceutical excipients.

The process is suitable for the preparation and purification of IFN-α from different species, e.g., human or animal IFN-α's. The host organism used for the preparation and purification may be a procaryote or eucaryote, e.g., *E. coli, B. subtilis* or *Saccharomyces cerevisiae,* preferably *E. coli.* The conditions of cultivation for the various host organisms are well known to those skilled in the art and are described in detail, e.g., in the textbooks of Maniatis et al. (*Molecular Cloning,* Cold Spring Harbor Laboratory, 1982) and Sambrook et al. (*Molecular Cloning—A Laboratory Manual,* 2nd. ed., Cold Spring Harbor Laboratory, 1989).

The process is particularly suitable for the preparation and purification of recombinant human IFN-α's. There are many types of recombinant human IFN-α's including but not limited to IFN-α1, IFNα2 (such as IFN-α2A, IFNα2B, IFN-α2C), IFNαII (also designated IFN-$α_{II}$ or omega interferon), and further natural and artificial allelic variants, molecules containing inversions, deletions, insertions and modifications (such as pegylated IFN's) as well as any hybrid or consensus IFN molecules obtainable from the afore-mentioned molecules.

The extraction of the expressed IFN-α can be carried out by any conventional means, but is preferably carried out using a chaotropic agent, especially a guanidinium salt. The preferred guanidinium salt is guanidinium hydrochloride (hereinafter also referred to as guanidinium HCl, Gu.HCl or Gu). The concentration of the guanidinium salt in the treatment of the host is not critical in that any effective amount may be used. It is preferred, however, that a 1 to 8 M, preferably a 7 to 8 M solution of the guanidinium salt in a pH range of from 2.0 to 8.0, preferably about pH 3.0, is used for extracting the expressed IFN-α.

Re-folding of the extracted IFN-α can be carried out by any conventional means, but is preferably carried out by suitably diluting the extraction solution with water or an aqueous buffer solution, for example, to a guanidinium salt concentration of about 0.1 to 1.0 M, preferably of about 0.6 M, in a pH range from 5.0 to 7.0, preferably about pH 6.0, and incubating the resulting mixture at 20 to 30° C. for about 16–20 hours.

As metal chelate chromatography columns there come into consideration cobalt, nickel, zinc or copper chelate columns which are known, e.g., from *Nature,* 258 (1975), 598–599 (Porath et al.), *J. Biol. Chem.,* 252 (1977), 5934–5935 (Edy et al.), and *J. Gen. Virol.,* 43 (1979), 701–706 (Chadha et al.). Preferably a copper chelate column is used. It is particularly preferred to use a copper chelate column with a copper chelate resin as described in European Patent No. 118 808 coupled to a carrier, such as agarose, of the formula:

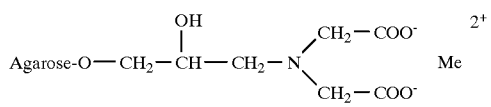

in which Me represents copper.

The copper chelate resin can be prepared in a known manner, as described, for example, by Hubert and Porath in *J. Chromatog.,* 198 (1980), 247, by treating agarose with epichlorohydrin, reacting the resulting epoxide with iminodiacetic acid disodium salt and converting the product into the copper salt by washing with a copper (II) salt solution, for example with copper sulphate. Epibromohydrin can be used in place of epichlorohydrin. As the agarose there is conveniently used a standardized product, preferably Sepharose® from Pharmacia, Uppsala, Sweden. Sepharose® CL-6B is especially preferred.

The preparation of a suitable copper chelate resin is illustrated in detail in European Patent No. 118 808.

Prior to the loading with IFN-α, the metal chelate column is conveniently equilibrated with an aqueous buffer (pH 5.0–8.0), preferably phosphate buffer, about pH 7.0. The equilibrating buffer (and also the elution buffer) can contain a denaturing agent or a chaotropic agent, for example, guanidinium hydrochloride, urea and/or a detergent, e.g., Tween 20. The addition of such a denaturing agent, chaotropic and/or detergent permits problem-free procedures even in the case of high interferon concentrations.

The elution is carried out in a manner known per se with an aqueous buffer solution, preferably with an acetate buffer, about pH 4.0.

As resin for hydrophobic interaction chromatography there is conveniently used a standardized product preferably a hydrophobic interaction resin from TOSO Haas GmbH, Stuttgart, FRG, preferably Toyopearl Butyl-650 (M).

Prior to the loading with IFN-α, the hydrophobic interaction chromatography column is conveniently equilibrated with an aqueous buffer (pH 5.0 to 7.0), preferably a phosphate buffer, about pH 6.5. The elution is carried out in a manner known per se with an aqueous buffer solution, preferably with an phosphate buffer, about pH 6.5.

As cation exchange chromatography columns there come into consideration carboxymethyl and hydroxy-sulfopropyl cation exchange chromatography columns. In the preferred practice of the present invention, a carboxymethyl cation exchange chromatography column is used, preferably with CM-Toyopearl 650(M) from TOSO Haas GmbH, Stuttgart, FRG. Other standardized products, e.g., from Merck, such as Fractogel EMD-CM 650, or from Whatman, such as CM-Cellulose 52, may also be used.

Prior to the loading of the eluate from the metal chelate or hydrophobic interaction chromatography column the cation exchange column is conveniently equilibrated with an aqueous buffer (pH 3.0–5.0), preferably with an acetate buffer, about pH 4.0. The elution is carried out in a manner known per se with an aqueous buffer solution, preferably with an acetate buffer, about pH 7.0.

As resin for anion exchange chromatography there is conveniently used a standardized product, preferably an anion exchange media from Pharmacia, Uppsala, Sweden. In the preferred practice of the present invention a quaternary aminoethyl anion exchange chromatography column is used, preferably with Q-Sepharose Fast Flow (FF) from Pharmacia. Other standardized products, e.g, from Bio Rad, such as Macro-Prep Q or High Q Anion Exchange Support, or from Merck, such as Fractogel EMD-TMAE 650, or similar gels from other suppliers may also be used.

Prior to the loading of the eluate from the anion exchange or the metal chelate column the anion exchange column is conveniently equilibrated with an aqueous buffer (pH 6.0–8.0), preferably an acetate buffer, about pH 7.5. The elution is carried out in a manner known per se with aqueous buffer solution, preferably with a pH gradient using acetate buffers of about pH 6.5 and 4.5.

As gel filtration resin there is conveniently used a standardized product, preferably gel filtration media from Pharmacia, Uppsala, Sweden, e.g. Sephadex (e.g., Sephadex G50 superfine), Sephacryl (e.g., Sephacryl S-200 High Resolution) and Sepharose type media. Superdex 75 is especially preferred. Gel filtration media from TOSO Haas GmbH, Stuttgart, FRG, e.g., TSK Toyopearl HW55 or similar gels from other suppliers may also be used.

The elution is carried out in a manner known per se with aqueous buffer solution, preferably using acetate buffers of about pH 5. Other conventional elution buffers that elute constituents which have a negative effect on the propoerties of IFN-α preparation may also be used in accordance with the invention.

In a preferred specific embodiment of the present invention, the novel process allowing production and purification of IFN-α is employed to purify IFN-α2A to homogeneity.

The specific process for producing homogeneous IFN-α2A comprises the following steps in combination:

(a) cultivating *E.coli* cells containing the IFN-α2A gene so as to express the IFN-α2A;

(b) extracting the expressed IFN-α2A using about 8 M guanidine hydrochloride;

(c) re-folding the extracted IFN-α2A by diluting the extraction solution with water to a guanidinium hydrochloride concentration of about 0.6M;

(d) subjecting the IFN-α2A to copper chelate affinity chromatography;

(e) subjecting the copper chelate purified IFN-α2A to carboxymethyl cation exchange chromatography;

(f) subjecting the IFN-α2A eluted from the carboxymethyl cation exchange chromatography to quaternary aminoethyl anion exchange chromatography; and (g) passing the IFN-α2A eluted from the quaternary aminoethyl anion exchange chromatography through a gel filtration column, preferably a Superdex 75 column.

Examples 1–4 further illustrate details and modifications of the specific process for producing IFN-α2A.

Vectors suitable for expression of IFN-α in host cells are described, for example, in the afore-mentioned European Patents Nos. 32 134, 43 980 and 211 148. Especially suitable vectors for expression of IFN-α2A in *E. coli* are plasmids of the pLIF-A-trp family, such as pLIF-A-trp 25, pLIF-A-trp 35 and pLIF-A-trp 45 (described in European Patents Nos. 43 980 and 211 148).

Alternatively, since the DNA sequences of genes coding for IFN-α's are known (European Patents Nos. 32 134, 43 980 and 211 148, *Interferon,* Vol. 1 (1984), A. Billiau (ed.), Elsevier Publishers B. V., Chapter III, pp. 61–78), DNA sequences coding for the IFN-α's in accordance with the present invention can be chemically synthesized using standard methods known in the art, e.g., by the phosphotriester method (Narang et al., in *Meth. Enzymol.,* 68, 90–108 (1979)) or by the phosphodiester method (Brown et al., *Meth. Enzymol.,* 68, 109–151 (1979)). The nucleotide sequences of the DNA fragments coding for the IFN-αs can be identical with those occuring in nature. There exists on the other hand the possibility that partially or completely different nucleotide sequences code for the same IFN-α's. If desired, there can be selected for the nucleotide sequences those codons which are also preferably used by the host organism for the expression of the polypeptide (Grosjean et al., *Gene,* 18, 199–209 (1982)). Care must, however, be taken that the thus-obtained DNA sequences do not contain partial sequences which make the construction of the expression vectors difficult, e.g., by introducing an undesired restriction enzyme cleavage site.

After the production of the DNA sequences which code for the IFN-α's, these can be incorporated according to known methods into any suitable expression vector which produces the requisite expression signals. Suitable vectors can be constructed from segments of chromosomal, non-chromosomal and synthetic DNA sequences such as, e.g., various known plasmids and phage DNAs. In this connection, reference can be made to the afore-mentioned textbook of Maniatis et al.

The expression vectors which contain the DNA sequences coding for the IFN-α's in accordance with the invention operatively linked with an expression control sequence can be incorporated in a manner known per se into any suitable host organism. The selection of a suitable host organism is determined by different factors which are known to the person skilled in the art. Thus, for example, compatibility with the chosen vector, toxicity of the expression product, expression characteristics, necessary biological safety precautions and costs play a role and a compromise between all of these factors must be found.

As already stated above, as suitable host organisms for the preparation and purification of IFN-α's in accordance with the process of the present invention there come into consideration procaryotic and eucaryotic host cells. Suitable procaryotic host cells include gram-negative and gram-positive bacteria, for example *E. coli* and *B. subtilis* strains, as well as Saccharomyces, for example *Saccharomyces cerevisiae*. Especially suitable procaryotic host organisms for use in the process of the present invention are *E. coli* strains W 3110 (ATCC No. 27325), 294 (ATCC No. 31446) and RR1 (ATCC No. 31343).

Eucaryotic host cells that could be used include, e.g., human Hela, H9 and Jurkat cells, mouse NIH3T3 and C127 cells, CV1 African green monkey kidney cells, quail QC1-3 cells, Chinese hamster ovary (CHO) cells, mouse L cells and the COS cell lines.

The present invention also relates to the pure and homogeneous IFN-α obtainable by the process of the present invention and its use in antitumor and/or antiviral treatment. Any conventional dosage, dosage form and dose rate for IFN-α may be used.

Having now generally described this invention, the same will become better understood by reference to the specific examples, which are included herein for purpose of illustration only and are not intended to be limiting unless otherwise specified, in connection with the figures.

The determination of the protein content was carried out according to the method of Lowry et al. (*J. Biol. Chem.,* 193, 265–275 (1951)) or by measuring optical densities at 280 nm wavelength ($OD_{280}$).

The analytical analysis of IFN-α2A preparations was carried out by means of RP-HPLC. RP-HPLC analysis was done at ambient temperature (20–22° C.), using Kontron equipment with two LC pumps 414-T, an UV detector Uvicon 722 LC and a programmer Model 220 or equivalent equipment.

Column: Bakerbond WP RP-18, 4.6 mm×25 cm

Mobile Phase: (A) 30% acetonitrile 0.2% TFA
(B) 80% acetonitrile 0.2% TFA

Flow rate: 0.9 ml/min.

| Gradient: | time | % B |
|---|---|---|
| | 0 | 29.0 |
| | 5 | 33.8 |
| | 20 | 38.0 |
| | 30 | 44.0 |
| | 40 | 61.0 |
| | 42 | 61.0 |
| | 50 | 29.0 |
| | 60 | 29.0 |

Detection: UV 210 nm

Injection: 15 μg of protein were loaded on the column.

The biomass containing IFN-α2A used as the starting material was obtained according to the methods described in European Patents Nos. 43980 and 211148.

EXAMPLE 1

Extraction and Refolding of IFN-α2A

A. Extraction of IFN-α2A out of biomass 1 part of biomass containing about 20–25% dry weight was extracted with 4 parts of extraction buffer containing 1–8 M guanidinium hydrochloride 50 mM Tris 0 or 2% Tween 20 pH 3.

Extraction was done for 3 hours at ambient temperature. Maximal yields of IFN-α2A after refolding were obtained by extraction using 7 to 8M guanidinium hydrochloride (yields 1.7 to 1.9 mg/g biomass, see FIG. 1A). Variation of the extraction time between 1 and 24 hours at optimal guanidinium hydrochloride concentrations resulted in an optimum between 1 and 4 hours (see FIG. 1B). Variation of the extraction pH between 3 and 7 under the upper optimised conditions yielded a maximal extraction yield at pH 3.0 (see FIG. 1C).

The content of IFN-α2A was determined by RP-HPLC as described above.

B. Refolding of IFN-α2A

Extracts prepared at room temperature by 3 hours extraction using

Figure 2C:
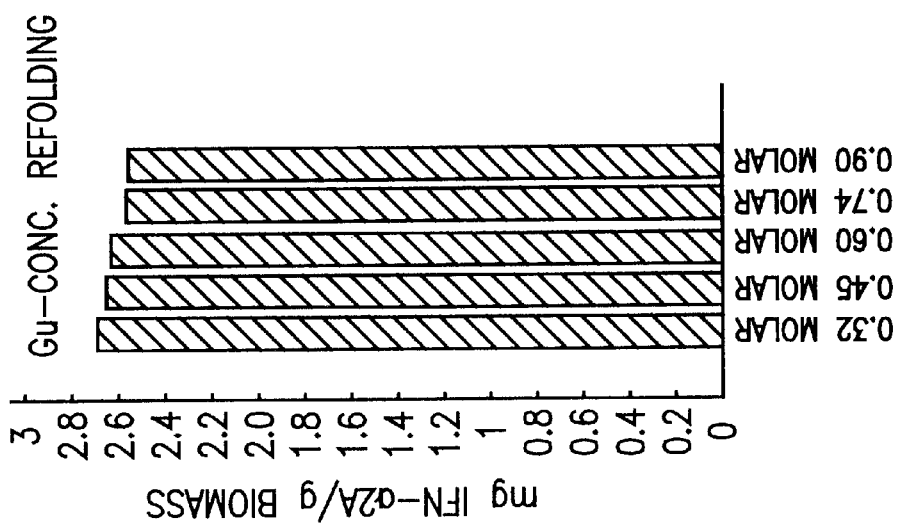
FIG. 2 shows the results of refolding of IFN-α2A subject to pH-values (A), dilution ratio (B) and guanidinium concentration (C).
Figure 2B:
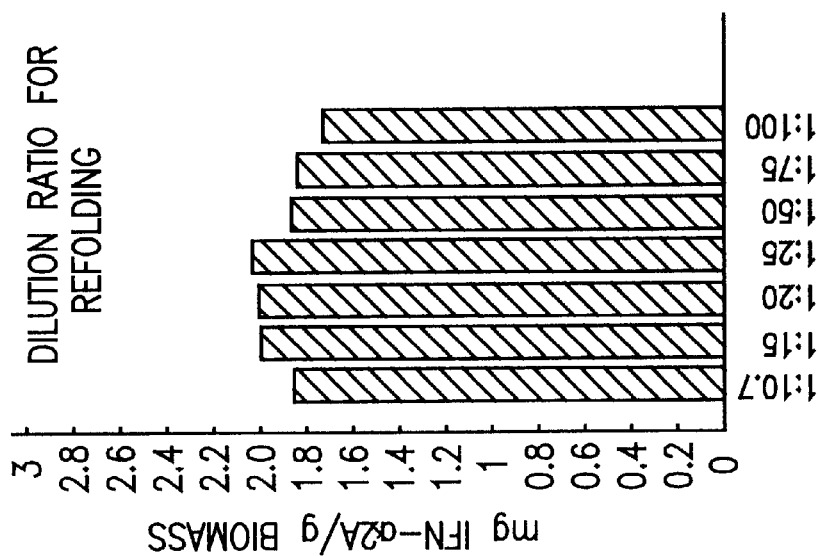
Figure 2A:
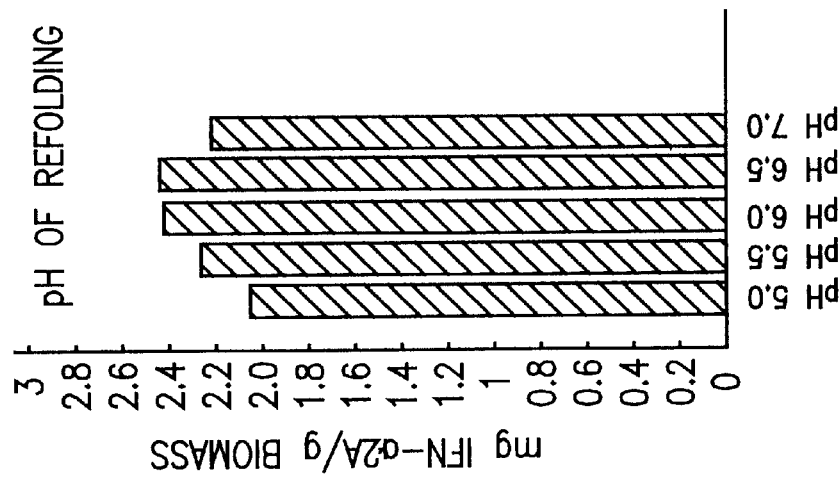

8 M guanidinium hydrochloride
50 mM Tris
2% Tween 20
pH 3 were diluted 1:20 into guanidinium hydrochloride containing buffers to give pH values between 5 and 7 and a guanidinium hydrochloride concentration of 0.6M. Diluted extracts were stored for about 72 hours at 4° C. Increasing amounts of refolded IFN-α2A could be detected during this time by RP-HPLC. Optimal yields were obtained at pH values between 6 and 6.5 (FIG. 2A). Variation of the dilution ratio under the upper conditions (pH 6) between 1:11 to 1:100 resulted in good yields at all dilutions (1.7 to 2.1 mg/g biomass), best results were obtained at 1:15 to 1:25 (2.0 to 2.1 mg/g, FIG. 2B). Variation of the guanidinium hydrochloride concentration under the upper conditions (ratio 1:20) resulted in yields between 2.5 to 2.7 mg/g biomass, best values (2.7 mg/g) were obtained at guanidinium hydrochloride concentrations between 0.32 and 0.6 M (FIG. 2C).

EXAMPLE 2

Production of Homogeneous IFN-α2A

A. Extraction 499 g biomass were extracted with 2 l extraction buffer (50 mM Tris, pH 3.0 containing 8 M guanidinium hydrochloride) for 2 hours at room temperature (RT). Then the extract was diluted with water to a Gu.HCl concentration of 0.6 M and the pH adjusted to 6. The diluted extract was kept overnight (16–20 hours) at room temperature to fold the interferon alfa-2a molecule properly. Cell debris were removed by centrifugation and the supernatant was further clarified by tangential flow microfiltration. A sample was taken for analysis.

B. Copper chelate affinity chromatography

At room temperature the clarified extract, pH 7, was loaded onto a 4 liter copper chelate column (d: 25 cm, h: 10 cm) equilibrated with buffer CC O. After washing with buffer CC O and CC 1, the interferon was eluted with buffer CC 2. A sample was taken for analysis. The column was regenerated with buffer CC 3 and sanitized with 0.5 N NaOH. All following steps were done in the cold room.

Buffer CC 0: 0.6 M Gu.HCl
    0.15 M NaCl
    20 mM $Na_2 HPO_4$
    0.1% Tween-20
    pH 7.0
Buffer CC 1: 0.15 M NaCl
    50 mM acetic acid
    0.1% Tween-20
    pH 5.0
Buffer CC 2: 0.15 M NaCl
    50 mM acetic acid
    0.1% Tween-20
    pH 4.0
Buffer CC 3: 0.15 M NaCl
    0.2M acetic acid
    0.1% Tween-20
    pH 5.0

C. Carboxymethyl cation exchange chromatography

After pH adjustment to 4.0, the eluate of the copper chelate column was loaded onto a 0.6 liters carboxymethyl cation exchange column (CM-Toyopearl 650 (M), TOSO Haas GmbH, Stuttgart, FRG; d: 5 cm, h: 30 cm) equilibrated with buffer CMF 0. After washing with buffer CMF 1, the interferon was eluted with buffer CMF 2. A sample was taken for analysis. The column was regenerated with buffer CMF 3 and sanitized with 0.5 N NaOH.

Buffer CMF 0: 75 mM acetic acid/sodium acetate,
    pH 4.0
Buffer CMF 1: 15 mM acetic acid/sodium acetate,
    pH 5.5
Buffer CMF 2: 30 mM acetic acid/sodium acetate,
    pH 7.0
Buffer CMF 3: 0.5M NaCl
    0.2M acetic acid D. Quaternary aminoethyl anion exchange chromatography The eluate from the cation exchange column was adjusted to pH 8 and loaded onto a 400 ml quaternary aminoethyl anion exchange column (Q-Sepharose Fast Flow (FF), Pharmacia, Uppsala, Sweden; d: 7 cm, h: 10 cm) equilibrated with buffer QS 0. After washing with buffer QS 1, the interferon was eluted with a pH gradient, buffer QS 2 to buffer QS 3 (pH 6.5 to 4.5). A sample was taken for analysis. The column was regenerated with 0.5 N NaOH.

Buffer QS 0: 0.3M ammonium acetate,
    pH 7.5
Buffer QS 1: 30 mM ammonium acetate,
    pH 7.6
Buffer QS 2: 25 mM ammonium acetate,
    pH 6.5
Buffer QS 3: 5 mM acetic acid,
    pH 4.5

E. Gel filtration chromatography

The eluate from the anion exchange chromatography was adjusted to pH 5.0, concentrated to a protein concentration of maximal 10 mg/ml using an Amicon YM10 ultrafiltration membrane and loaded onto a 6 liter gel filtration column (Superdex 75, Pharmacia, Uppsala, Sweden; d: 9 cm, h: 90 cm). The gel filtration column was sanitized with 0.1 N NaOH and equilibrated and developed with the interferon alfa-2a bulk buffer. Samples were taken for analyses.

IFN-2a bulk buffer: 25 mM ammonium acetate
    120 mM sodium chloride
    pH 5.0

Figure 3:
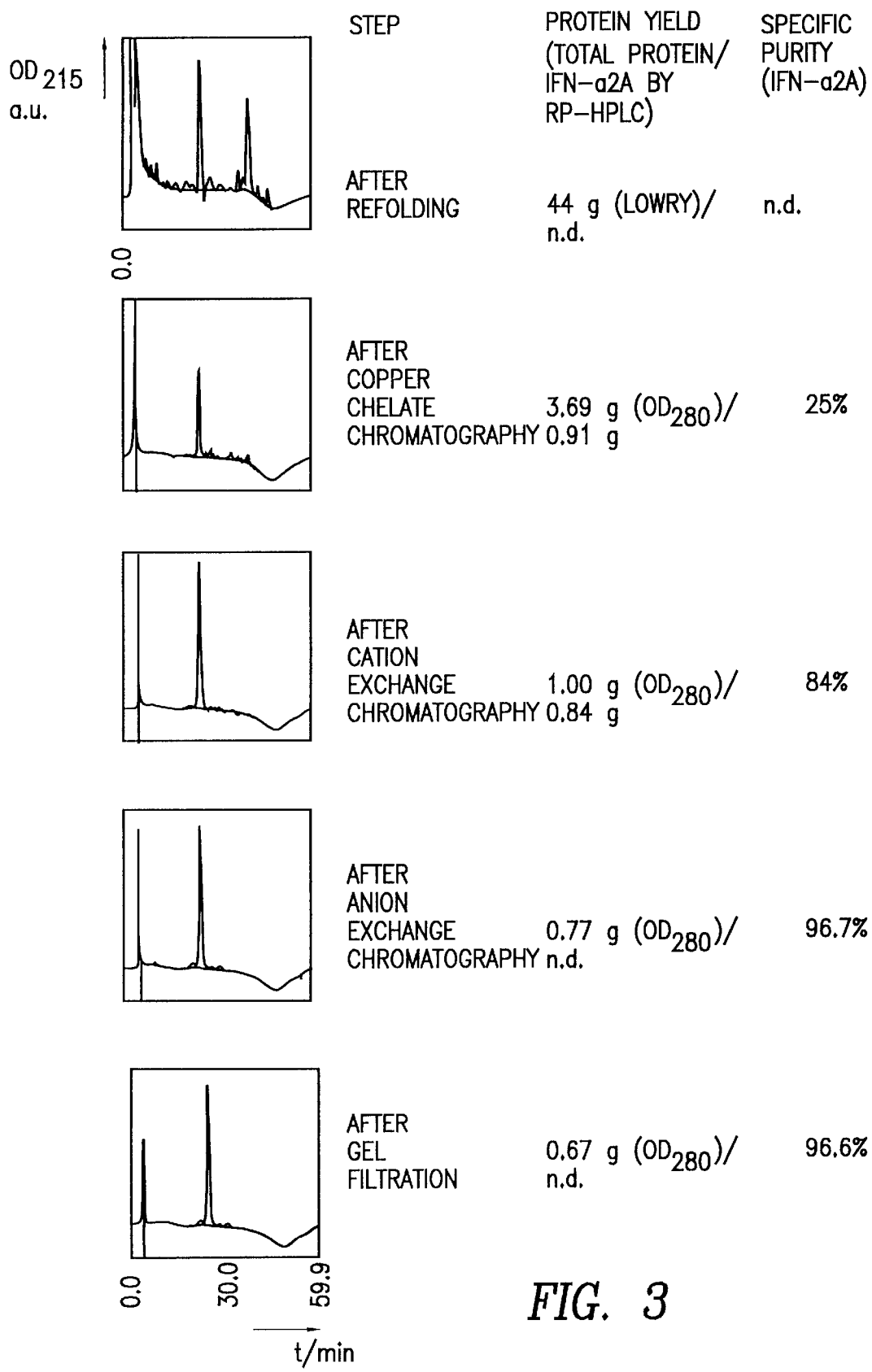
FIG. 3 shows the RP-HPLC analyses of protein samples taken after different process steps. a.u. denotes arbitrary units.

The results of the analyses of the samples taken after the above process steps are shown in FIG. 3 and Table I below. A summary of analytical data as to the final IFN-α2A product is given in Table II below.

TABLE 1

Purification of IFN-α2A

| | | | |
|---|---|---|---|
| A. | Extraction: | biomass | 499 g |
| | | protein extr. (Lowry) | 44 g |
| B. | Cu chelate chromatography | | |
| | eluate: | Protein (OD280) | 3.69 g |
| | | IFN-α2A (RP-HPLC) | 0.91 g |
| | | specific purity* | 25% |
| C. | Cation exchange chromatography | | |
| | eluate: | protein (OD280) | 1.00 g |
| | | IFN-α2A (RP-HPLC) | 0.84 g |
| | | specific purity* | 84% |
| D. | Anion exchange chromatography | | |

TABLE 1-continued

Purification of IFN-α2A

| | | | |
|---|---|---|---|
| eluate: | protein (OD280) | 0.77 g | |
| | IFN-α2A (RP-HPLC) | 96.7% | |
| E. Gel filtration | | | |
| eluate: | protein (OD280) | 0.67 g | |
| | IFN-α2A (RP-HPLC) | 96.6% | |
| Yield: | g IFN-α2A/kg Biomass | 1.3 g/kg | |

*specific purity: IFN-α2A (RP-HPLC)/total protein (OD280)

TABLE II

Analytical Data of IFN-α2A (final product)

| Gel filtration eluate | IFN-α2A |
|---|---|
| Protein: protein total OD280 | 0.67 g |
| concentration OD280 | 1.08 g/l |
| E280/260 | 1.85 |
| SDS-PAGE | >99% |
| RP-HPLC | 96.6% |
| Specific activity | $2.7 \times 10^8$ U/mg |
| AAS; Cu | <19 ppm |
| Bacterial endotoxins | <0.09 EU/mg |
| Microbial contamination | <0.1/ml |

EXAMPLE 3

1st Step in the Purification of IFN-α2A by Hydrophobic Interaction Chromatography Extracts were prepared by mixing 1 part of biomass with 4 parts of 7 M guanidinium hydrochloride 50 mM Tris pH 3

After 3 hours of extraction at RT the extract was diluted 1:20 by:

20 mM NaH2PO4

150 mM NaCl pH 6.5

After 16–30 hours of refolding (RT) 33 Vol % of 4 M (NH4)$_2$SO$_4$ were added and the pH was adjusted to 6.5. After centrifugation at 6000 g for 20 minutes the extract was applied to a column of Toyopearl Butyl-650M (TOSO Haas GmbH, Stuttgart, FRG; RT), which had been equilibrated with 5 column volumes of:

50 mM NaH2PO4

1M (NH4)2SO4 pH 6.5

133 ml of extract were applied per ml of gel. The column was washed with 5 column volumes of equilibration buffer and eluted with 50 mM Na$_2$HPO$_4$, pH 6.5 at a flow rate of 100–200 cm/h at RT. The specific purity was 25–30%.

EXAMPLE 4

Purification of IFN-α2A Using a Strong Cation Exchanger as a 2nd or 3rd Purification Step 2 mg per ml gel of a prepurified mixture of IFN-α2A adjusted to pH 4 and a conductivity lower than 15 mS were loaded on a column of S-Source (Pharmacia), which had been preequilibrated with 75 mM Na-acetate, pH 4.0. In the following the column was washed with 5 column volumes of equilibration buffer and then with 12 column volumes of buffer A. A linear gradient of 100 column volumes from 100% buffer A, 0% B to 100% buffer B was used for elution (buffer A=15 mM KH$_2$PO$_4$, pH 4.0; buffer B=30 mM KH$_2$PO$_4$, pH 6.6). Elution can also be performed using an elution step with 17 mM KH$_2$PO$_4$, pH 6.05. The flow rate is 100 cm/hour and the column is run either at room temperature or 4° C. Baseline separation between the Mf1 form and the MF2 form (acetylated and hydroxyacetylated IFN-α2A is obtained by this method. A nearly baseline separation is also obtained using S HyperD gel (Sepracor) under the same conditions.

We claim:

1. A process for purifying IFN-α to homogeniety, comprising:

(a) extracting recombinant cell culture which expresses IFN-α with a 7–8 M aqueous solution of a guanidinium salt at about pH 3 to obtain an aqueous solution containing denatured IFN-α and other co-produced proteins;

(b) refolding the IFN-α by diluting said aqueous solution to a guanidinium salt concentration of 0.1 to 1.0 M and a pH of 5.0 to 7.0 with water or an aqueous buffer solution;

(c) thereafter subjecting the proteins in said aqueous solution from step (b) to metal chelate chromatography or hydrophobic interaction chromatography, and to cation exchange chromatography by either:

(i) passing the aqueous solution containing the IFN-α through a metal chelate chromatography column or a hydrophobic interaction chromatography column whereby the IFN-α is captured on said column and eluting the IFN-α from said column with a first aqueous buffer solution to obtain IFN-α in said first aqueous buffer solution; and thereafter (ii) passing the first aqueous buffer solution containing the IFN-α through a cation exchange chromatography column whereby the IFN-α is captured on said column and eluting the IFN-α from said column with a second aqueous buffer solution to obtain IFN-α in said second aqueous buffer solution;

or (i) passing the first aqueous buffer solution containing the IFN-α through a cation exchange chromatography column whereby the IFN-α is captured on said column and eluting the IFN-α from said column with a first aqueous buffer solution to obtain IFN-α in said first aqueous buffer solution; and thereafter (ii) passing the first aqueous buffer solution containing the IFN-α through a metal chelate chromatography column or a hydrophobic interaction chromatography column whereby the IFN-α is captured on said column and eluting the IFN-α from said column with a second aqueous buffer solution to obtain IFN-α in said second aqueous buffer solution;

(d) thereafter passing the second aqueous buffer solution obtained from step (c) containing the IFN-α through an anion exchange chromatography column whereby the IFN-α is captured on said column and eluting the IFN-α from said column with a third aqueous buffer solution to obtain IFN-α in said third aqueous buffer solution; and (e) thereafter passing said third aqueous buffer solution obtained from step (d) containing the IFN-α through a gel filtration chromatography column whereby the IFN-α is captured on said column and eluting the IFN-α from said column with a fourth aqueous buffer solution to obtain homogenous IFN-α in said fourth aqueous buffer solution.

2. The process of claim 1 wherein the aqueous solution containing the IFN-α and other co-produced proteins has been subjected to metal chelate chromatography and to cation exchange chromatography.

3. The process of claim 2 wherein the metal chelate chromatography is carried out prior to the cation exchange chromatography.

4. The process of claim 3 wherein the metal chelate chromatography is copper chelate chromatography.

5. The process of claim 4 wherein the anion exhange chromatography is quarternary aminoethyl anion exchange chromatography.

6. The process of claim 5 wherein said third aqueous buffer solution is an aqueous acetate buffer solution.

7. The process of claim 6 wherein the pH of said third aqueous buffer solution is a pH gradient from about pH 6.5 to about pH 4.5.

8. The process of claim 7 wherein the IFN-α is IFN-α2A.

9. The process of claim 3 wherein the cation exchange chromatography is carried out prior to the metal chelate chromatography.

10. The process of claim 9 wherein the metal chelate chromatography is copper chelate chromatography.

11. The process of claim 10 wherein the anion exhange chromatography is quarternary aminoethyl anion exchange chromatography.

12. The process of claim 11 wherein said third aqueous buffer solution is an aqueous acetate buffer solution.

13. The process of claim 12 wherein the pH of said third aqueous buffer solution is a pH gradient from about pH 6.5 to about pH 4.5.

14. The process of claim 13 wherein the IFN-α is IFN-α2A.

15. The process of claim 1, wherein the aqueous solution containing the IFN-α with co-produced proteins has been subjected to hydrophobic interaction chromatography and to cation exchange chromatography.

16. The process of claim 15 wherein the step of hydrophobic interaction chromatography is carried out prior to the step of cation exchange chromatography.

17. The process of claim 16 wherein the anion exhange chromatography is quarternary aminoethyl anion exchange chromatography.

18. The process of claim 17 wherein said third aqueous buffer solution is an aqueous acetate buffer solution.

19. The process of claim 18 wherein the pH of said third aqueous buffer solution is a pH gradient from about pH 6.5 to about pH 4.5.

20. The process of claim 19 wherein the IFN-α is IFN-α2A.

21. The process of claim 20 wherein the step of cation exchange chromatography is carried out prior to the step of hydrophobic interaction chromatography.

22. The process of claim 21 wherein the anion exhange chromatography column is a quarternary aminoethyl anion exchange chromatography column.

23. The process of claim 22 wherein said third aqueous buffer solution is an aqueous acetate buffer solution.

24. The process of claim 23 wherein the pH of said third aqueous buffer solution is a pH gradient of from about pH 6.5 to about pH 4.5.

25. The process of claim 24 wherein the IFN-α is IFN-α2A.

26. A process for obtaining an aqueous solution containing IFN-α and other co-produced proteins from a recombinant cell culture which expresses IFN-α, which process comprises:

(a) extracting the recombinant cell culture with a 7–8 M aqueous solution of a guanidinium salt at about pH 3; and (b) refolding the IFN-α by diluting the aqueous solution to a guanidinium salt concentration of 0.1 to 1.0 M and a pH of 5.0 to 7.0 with water or an aqueous buffer solution;

whereby the aqueous solution containing IFN-α and other co-produced proteins is obtained.

27. The process of claim 26 wherein the guanidinium salt is guanidinium hydrochloride.

* * * * *

UNITED STATES PATENT AND TRADEMARK OFFICE
CERTIFICATE OF CORRECTION

PATENT NO. : 6,005,075
DATED : December 21, 1999
INVENTOR(S) : Urs Ettlin et al.

It is certified that error appears in the above-identified patent and that said Letters Patent is hereby corrected as shown below:

In claim 9, column 13, line 21, delete "claim 3" and insert therefor

-- claim 2 --.

Signed and Sealed this

Eighteenth Day of July, 2000

Attest:

Q. TODD DICKINSON

*Attesting Officer*  *Director of Patents and Trademarks*